US 6,623,699 B1

(12) United States Patent
Pack et al.

(10) Patent No.: US 6,623,699 B1
(45) Date of Patent: Sep. 23, 2003

(54) ANALYZING SYSTEM FOR HIGH ACCURACY NITROGEN DETERMINATION

(75) Inventors: Brian W. Pack, Coloma, MI (US); Carlos Guerra, Berrien Springs, MI (US); Peter M. Willis, Benton Harbor, MI (US); Joel C. Mitchell, Bridgman, MI (US)

(73) Assignee: Leco Corporation, St. Joseph, MI (US)

( * ) Notice: Subject to any disclaimer, the term of this patent is extended or adjusted under 35 U.S.C. 154(b) by 479 days.

(21) Appl. No.: 09/714,480

(22) Filed: Nov. 15, 2000

(51) Int. Cl.[7] .................. G01N 31/12; G01N 33/00
(52) U.S. Cl. .................. 422/80; 422/78; 422/79; 436/106; 436/114; 436/115; 436/116; 436/117; 436/118; 436/122; 436/127; 436/133; 436/134; 436/136
(58) Field of Search .................. 422/80, 79, 78; 436/106, 127, 133, 134, 136, 122, 114–118

(56) References Cited

U.S. PATENT DOCUMENTS

| | | | | |
|---|---|---|---|---|
| 3,934,991 A | * | 1/1976 | Frain et al. .................. 96/135 |
| 4,272,248 A | * | 6/1981 | Neti .................. 436/122 |
| 4,290,296 A | | 9/1981 | Bredeweg et al. | |
| 4,525,328 A | | 6/1985 | Bredeweg | |
| 4,569,918 A | * | 2/1986 | Moore et al. .................. 436/122 |
| 4,573,910 A | | 3/1986 | Bredeweg | |
| 4,622,009 A | | 11/1986 | Bredeweg | |
| 4,840,913 A | * | 6/1989 | Logothetis et al. .................. 436/116 |
| 5,851,293 A | * | 12/1998 | Lane et al. .................. 118/715 |
| 6,207,460 B1 | * | 3/2001 | Kishkovich et al. .................. 436/106 |

* cited by examiner

Primary Examiner—Jill Warden
Assistant Examiner—Brian Sines
(74) Attorney, Agent, or Firm—Price, Heneveld, Cooper, DeWitt & Litton

(57) ABSTRACT

An analyzer compensates for gas flow perturbations by providing a makeup flow of carrier gas to maintain the pressure and/or flow rate of analyte and inert gas through a detector constant such that a accurate determination of a low concentration of an analyte in the presence of a high concentration of a second analyte can be accurately determined. In one embodiment, a carrier gas is introduced through a valve responsive to the detected pressure in the gas flow stream between a scrubber and a subsequent detector for maintaining the pressure constant during an analysis. In another embodiment of the invention, a flow transducer is positioned in the gas flow path between the scrubber and detector and coupled to a flow control valve coupled to introduce carrier gas as a function of detected gas flow such that the flow rate of gas into the detector is maintained constant.

15 Claims, 3 Drawing Sheets

ANALYZING SYSTEM FOR HIGH ACCURACY NITROGEN DETERMINATION

BACKGROUND OF THE INVENTION

The present invention relates to analytical instruments and particularly instruments using an inert carrier gas in fusion or combustion furnaces for determining low concentrations of one analyte in the presence of high concentrations of another analyte.

In analytical instruments, typically a sample to be analyzed, such as a solid, liquid, or gas sample, is combusted in a furnace and subsequently the byproducts of combustion are swept by an inert gas, such as helium, into an oxidizer which converts, for example, carbon monoxide from the furnace into carbon dioxide for subsequent infrared detection. In order to analyze substances other than carbon dioxide (representative of the oxygen content of a sample), it is necessary to scrub and remove the carbon dioxide from the carrier stream so that the remaining analytes, such as nitrogen, can be measured by a subsequent detector, such as a thermal conductivity cell located downstream of the scrubber. With such systems, however, the scrubbing of carbon dioxide or other gas from the carrier stream reduces the pressure and flow rate of the carrier gas and remaining analytes as it approaches subsequent detectors for determining the remaining analyte. These perturbations in pressure and resulting flow rate result in inaccurate measurements of analytes subsequent to the scrubbing operation. In an oxygen/nitrogen analyzer, for example, the nitrogen, which is measured downstream of the scrubber with a thermal conductivity cell, is adversely affected and can result in readings which have a significant error. The error, for example, could be as high as 35 ppm (parts per million) for a nitrogen sample having a 5 ppm concentration in a sample having a high oxygen concentration of 50,000 ppm.

Although attempts have been made to overcome this problem using a split stream of analytes, such systems require a more complex and expensive flow system, and it is difficult to maintain the ratio of analytes split into two flow paths constant. Further, the analytical time is increased significantly as in the carrier gas consumption. Also the resultant accuracy, although improved, remains erroneous when measuring a low concentration analyte in combination with a high concentration analyte.

As a result, there exists a need for a relatively economical analysis system in which a relatively small concentration of an analyte in the presence of a higher concentration of a second analyte can be accurately determined without interference due to perturbations in the pressure or flow of the carrier-gas analyte stream.

SUMMARY OF THE INVENTION

The system of the present invention overcomes the problems of prior art analyzers by providing a compensation system for providing a makeup flow of carrier gas to maintain the pressure and/or flow rate of the stream of analyte and inert gas to a detector constant such that a accurate determination of a low level of an analyte can be accurately determined. In one embodiment of the invention, a carrier gas is introduced through a controlled valve responsive to a detected pressure in the gas flow stream between a scrubber and a subsequent detector for maintaining the pressure constant during an analysis. In another embodiment of the invention, a flow transducer is positioned in the gas flow path between the scrubber and detector and coupled to a flow control valve to introduce carrier gas as a function of detected gas flow such that the flow rate of gas into the detector is maintained constant. In either embodiment, a relatively low level of analyte, such as nitrogen, in the presence of a relatively high concentration of another analyte, such as oxygen, can be accurately determined utilizing a flow system which has a minimal number of components. Such a system provides greatly improved accuracy for the economical measurement of a relatively low level of analyte in the presence of a second analyte having a higher concentration.

These and other features, objects and advantages of the present invention will become apparent upon reading the following description thereof together with reference to the accompanying drawings.

DETAILED DESCRIPTION OF THE PREFERRED EMBODIMENT

Figure 1:
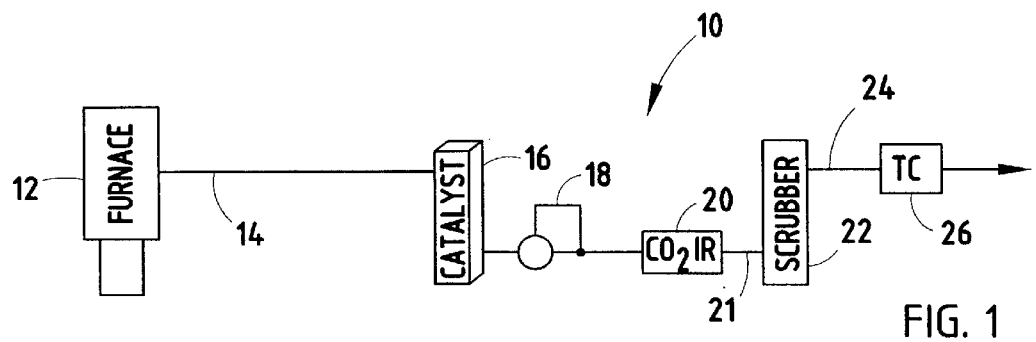
FIG. 1 is a schematic diagram of a prior art analyzer.

FIG. 1 shows a prior art analyzer 10 which includes a furnace 12, such as an EF400 furnace commercially available from Leco Corporation of St. Joseph, Mich., although the furnace can be an induction furnace, a resistance heating furnace, or other type of furnace which combusts a gas, liquid or solid sample. A carrier gas stream is introduced into the furnace such that at an outlet conduit 14, a mix of inert carrier gas (such as helium) and analytes (such as oxygen and nitrogen) are carried to be subsequently detected. The gas stream flows through a catalyst 16 which converts carbon monoxide (CO) to carbon dioxide ($CO_2$) for subsequent detection by a $CO_2$ infrared detector 20 to provide a measurement of the oxygen content in a sample. A flow controller 18 is positioned between a catalytic converter 16 and the infrared detector 20 to maintain the flow rate at about 450 cc/minute.

The stream of analytes in conduit 21 include carbon dioxide and typically another analyte(s), as for example nitrogen, flow into a scrubber 22 which scrubs or removes the carbon dioxide such that the remaining nitrogen in conduit 24 can be detected by a thermal conductivity cell 26. Suitable instrumentation, such as used in the commercially available TC 436 DR instrument manufactured by Leco Corporation of St. Joseph, Mich., can be coupled to the infrared detector 20 and the output 27 of thermal conductivity cell 26 to provide an operator with a readout of the concentration of, for example, oxygen and nitrogen in a sample.

Figure 2:
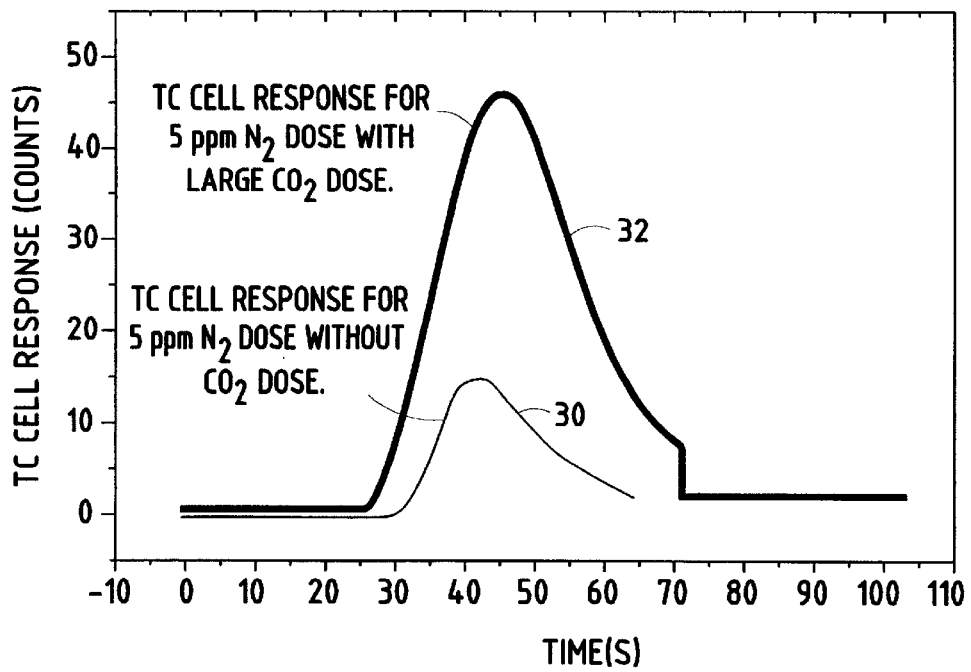
FIG. 2 is a diagram illustrating the inaccuracies of results utilizing the analyzer of FIG. 1 when a relatively low level of analyte is in a sample including a high concentration of a second analyte.

In FIG. 2, a readout from the analyzer is shown and illustrates the inaccuracies when using the analyzer of FIG.

1. In graphs 30 and 32 of FIG. 2, the nitrogen concentration is 5 ppm and, in the case of graph 30, no oxygen is present, resulting in no $CO_2$ after the scrubber. Thus, in graph 30, where, for example, the nitrogen concentration may be 5 ppm nitrogen is accurately read by the thermal conductivity cell 26 at a level of, for example, 15 counts detected by the thermal conductivity cell at the peak of the curve shown in FIG. 2. In the presence of oxygen, however, resulting in a high $CO_2$ concentration, the same 5 ppm of nitrogen results in an entirely different response by the detector, such as cell 26, as shown by graph 32. In graph 32, a 1 gram sample of steel having a 1.76% oxygen content yielded a 12 ppm nitrogen concentration result for the sample which, in fact, had a nitrogen concentration of 5 ppm. As shown by graph 32, the pressure and flow perturbations at the scrubber 22 eliminating the carbon dioxide from the flow stream results in a greatly increased readout level (47 counts) of nitrogen where in both instances the nitrogen concentration is the same. Thus, as seen in FIG. 2, depending upon the amount of oxygen present in a sample, a relatively low level of nitrogen in the same sample results in an entirely different and inaccurate response by the thermal conductivity cell typically employed for the detection of nitrogen.

Figure 3:
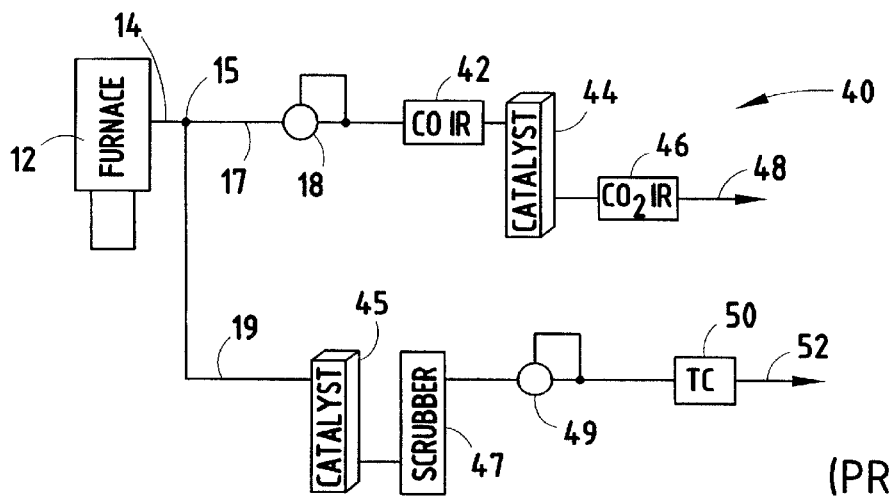
FIG. 3 is a schematic diagram of a prior art analyzer employing a split flow path employed to reduce the inaccuracies of the analyzer of FIG. 1.

In order to overcome this problem, a split ratio analyzer 40 shown in FIG. 3 has been employed in which again a conventional furnace 12 (the same reference numerals are used for the same or equivalent elements in the various figures) is employed and has an output conduit 14 to provide a carrier gas stream with combusted analytes such as carbon monoxide and nitrogen. The stream is split at junction 15 into flow paths 17 and 19 with path 17 passing through a flow controller 18 to a carbon monoxide infrared detector 42 having a signal output 43 and subsequently to a catalyst 44 for converting carbon monoxide to carbon dioxide for subsequent detection by an infrared detector 46 providing an output signal at conductor 48 to an analytical instrument, such as the TC 436 DR, for displaying the results to an operator. The branch 19 of the split stream contains the same gaseous element byproducts of combustion which flow through a catalyst 45 which converts the carbon monoxide to carbon dioxide subsequently scrubbed from the system by scrubber 47 with the remaining analytes flowing through flow controller 49 to a thermal conductivity cell 50 for reading the concentration of an analyte, such as nitrogen, remaining in the stream of gases from scrubber 47. The thermal conductivity cell provides output signals at output conductor 52 in the form of a digital signal (such as shown in FIG. 2), representing the concentration of an analyte, such as nitrogen, in the gas stream from scrubber 47. In this system where high levels of oxygen are present, detector 42 provides an initial concentration reading of oxygen converted to carbon monoxide.

Depending on the concentration of carbon dioxide, scrubber 47, as in the analyzer of FIG. 1, will decrease the back pressure and affect the flow rate in conduits 17 and 19 despite the utilization of flow controllers 18 and 49. Thus, it is difficult to maintain the ratio of flow rates in conduits 17 and 19 constant. Further, the split flow system is significantly more complex and, therefore, expensive since it requires more "plumbing". Also, the analysis time is increased significantly in view of the reduced amount of flow of gases through the split stream from the furnace 12. Although the accuracy of this system is improved over that of the FIG. 1 analyzer, errors remain when analyzing samples having a low concentration of one analyte and a high concentration of another analyte.

In order to overcome the inaccuracies inherent in the systems of FIGS. 1 and 3 and the complexities and costs of the split system shown in FIG. 3, the system of the present invention employs a carrier makeup stream to control the downstream pressure and flow rate after a scrubbing or other gas flow perturbation event such that the flow of carrier gas and analyte remains substantially constant for a second analyte after the first analyte has been scrubbed from the stream. The theory of operation of the system follows the Dalton's law of partial pressure in a system in which:

$$\text{Pressure}_{total\ before\ scrubber} = P_{CO_2} + P_{N_2} + P_{He} \quad \text{Formula 1}$$

$$\text{Pressure}_{total\ after\ scrubber} = P_{N_2} + P_{He} \quad \text{Formula 2}$$

Figure 4:
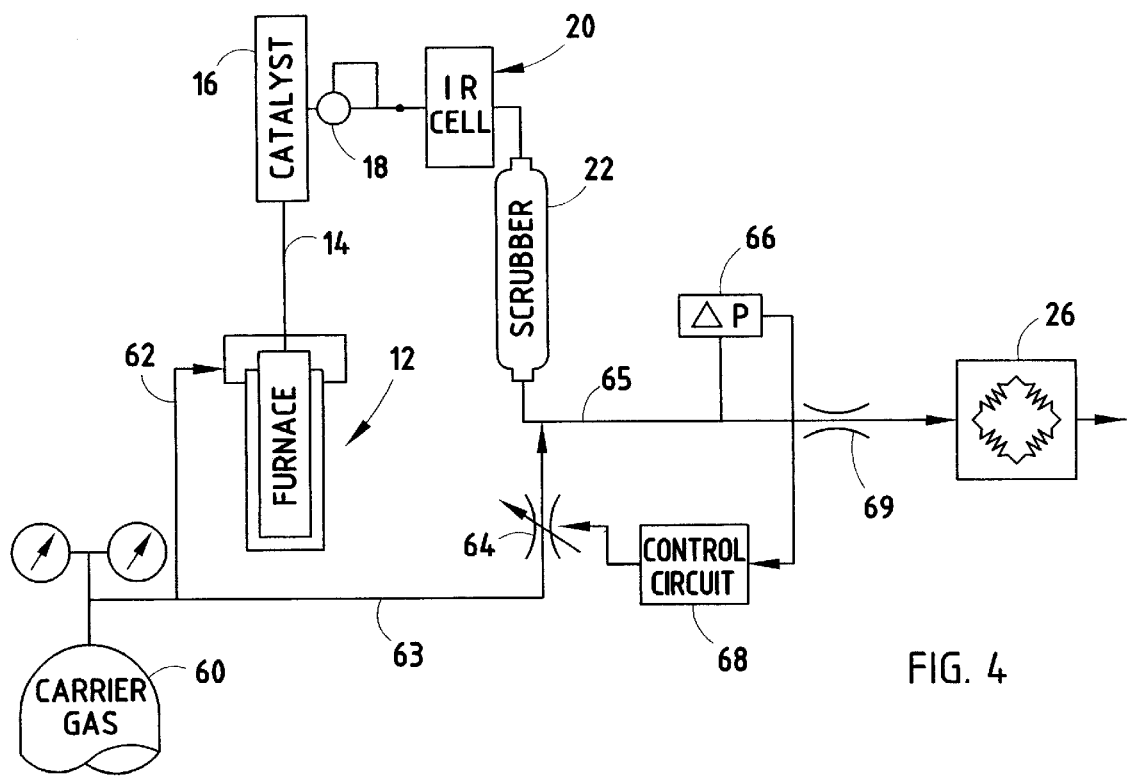
FIG. 4 is a schematic diagram of an analyzer of a first embodiment of the present invention.
Figure 5:
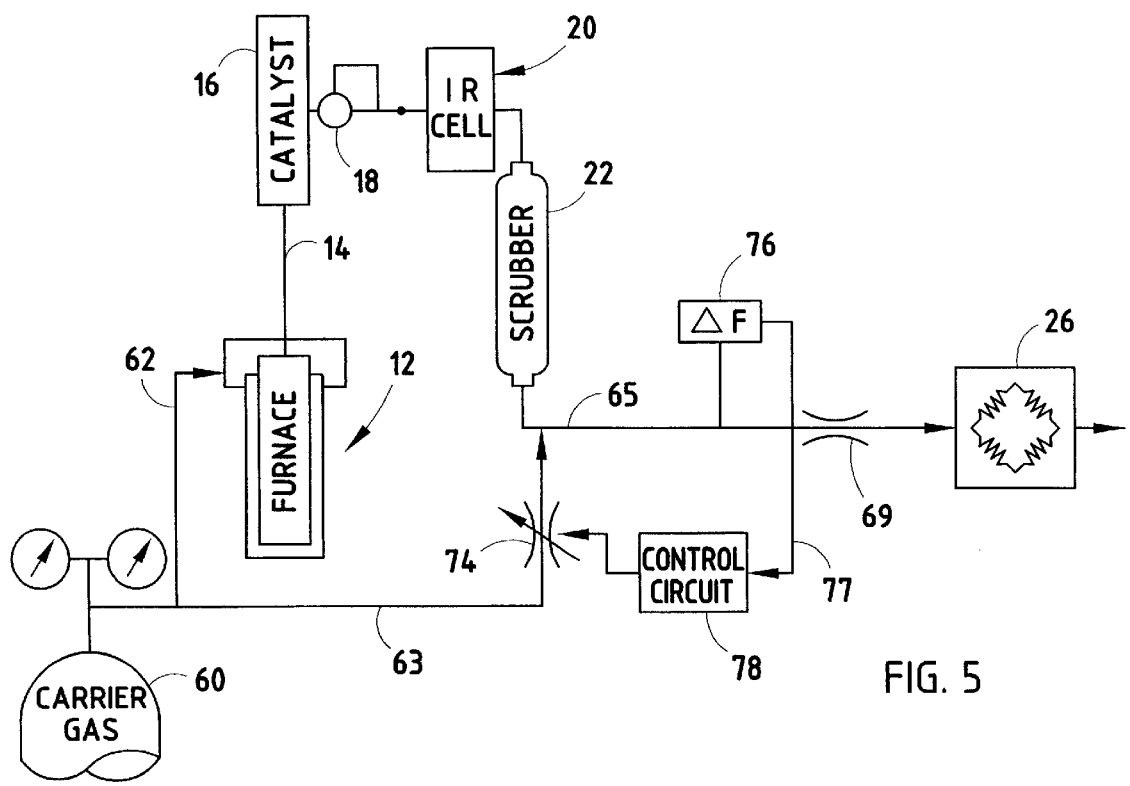
FIG. 5 is a schematic diagram of an analyzer of a second embodiment of the present invention.

As can be seen from the equations shown above, as the partial pressure due to the carbon dioxide, for example, in an oxygen/nitrogen analyzer is removed from the scrubber, the pressure after the scrubber is that provided by nitrogen and the helium carrier gas which will be significantly reduced when high concentrations of oxygen result in large amounts of carbon dioxide in the stream. In order to maintain the pressure constant and, therefore, the flow constant, a makeup carrier gas is introduced after the scrubber as shown in the systems of FIGS. 4 and 5 and described below, resulting in the following equation:

$$\text{Pressure}_{before\ scrubber} = \text{Pressure}_{with\ compensation} = P_{He\ Makeup\ Stream} + P_{N_2} + P_{He} \quad \text{Formula 3}$$

where the pressure represented by the helium makeup stream compensates for the pressure drop due to the scrubbing of carbon dioxide from the carrier gas stream.

In a typical analysis, the flow rate of carrier gas prior to an analysis into the thermal conductivity cell 26 (shown in FIGS. 1 and 3) typically will be 450 cc per minute at a pressure of 5 psi. When analyzing a sample having a high oxide (i.e., oxygen) content, such as glass, as the analysis is begun nearly 80% of the gas may be converted to $CO_2$ which, when scrubbed, drops the pressure at the output of the scrubber from 5 psi to about 3 psi, reducing the flow rate of the remaining analyte, such as nitrogen, through the thermal conductivity cell 26 to 90 cc per minute, as an example. This results in the thermal conductivity cells of the prior art providing an erroneous high reading of a low concentration of a second analyte, such as nitrogen.

In the system of FIGS. 4 and 5 in this scenario, the stream of makeup helium introduced before an analysis is 10 cc for a total flow of purging helium and makeup helium of about 460 cc per minute. During an analysis when the flow rate and pressure tends to be greatly reduced by the scrubbing operation (90 cc per minute and 3 psi, respectively as one example), the first and second embodiments of the present invention supplies makeup inert gas to compensate for this effect. In the analyzers of the present invention, for example, 370 cc per minute of makeup helium is introduced such that the total flow rate through the thermal conductivity cell remains at 460 cc per minute or maintains the pressure at 5 psi to, in effect, maintain the flow rate constant depending upon the type of sensor employed in the analyzer of the present invention. Having described the theory of operation and an example of the makeup carrier stream, a description of the analyzers of the present invention follows.

In the first embodiment shown in FIG. 4, a furnace 12 is employed and supplied with a carrier gas from a source 60, such as helium, which introduces gas into furnace 12 through a conduit 62 and to an electronic proportional control valve 64 via conduit 63 to a first conduit 65 on the output side of scrubber 22 in the flow path of byproducts of combustion in conduit 14 which flow through a catalyst 16, as in the first embodiment, a flow controller 18, and an infrared detector 20 for detecting the oxygen concentration through detection of carbon dioxide concentration. The pressure in conduit 65, which extends between detector 20 and detector 26, is detected by a pressure transducer 66 which provides an electrical control signal to control circuit 68 which, in turn, provides a signal to control valve 64 to maintain the pressure in conduit 65 relatively constant at, for example, 5 psi regardless of the concentration of carbon dioxide and, therefore, the tendency of scrubber 22 to significantly drop the pressure as shown by Formulas 2 and 3 above.

Thus, in the case where partial pressure due to carbon dioxide is relatively high, the pressure drop, as shown by Formula 2 results in helium makeup gas from conduit 63 being increased to maintain the pressure in conduit, and, therefore, the gas flow rate through the thermal conductivity cell 26, which is coupled to the conduit 65 through a 10,000 cc per minute flow restrictor 69 relatively constant regardless of the concentration of oxygen converted to carbon dioxide by scrubber 22. In a high oxygen content sample, the pressure compensation will, for example, maintain the pressure in conduit at about 5 psi where without such compensation the pressure would drop to about 3 psi.

Figure 6:
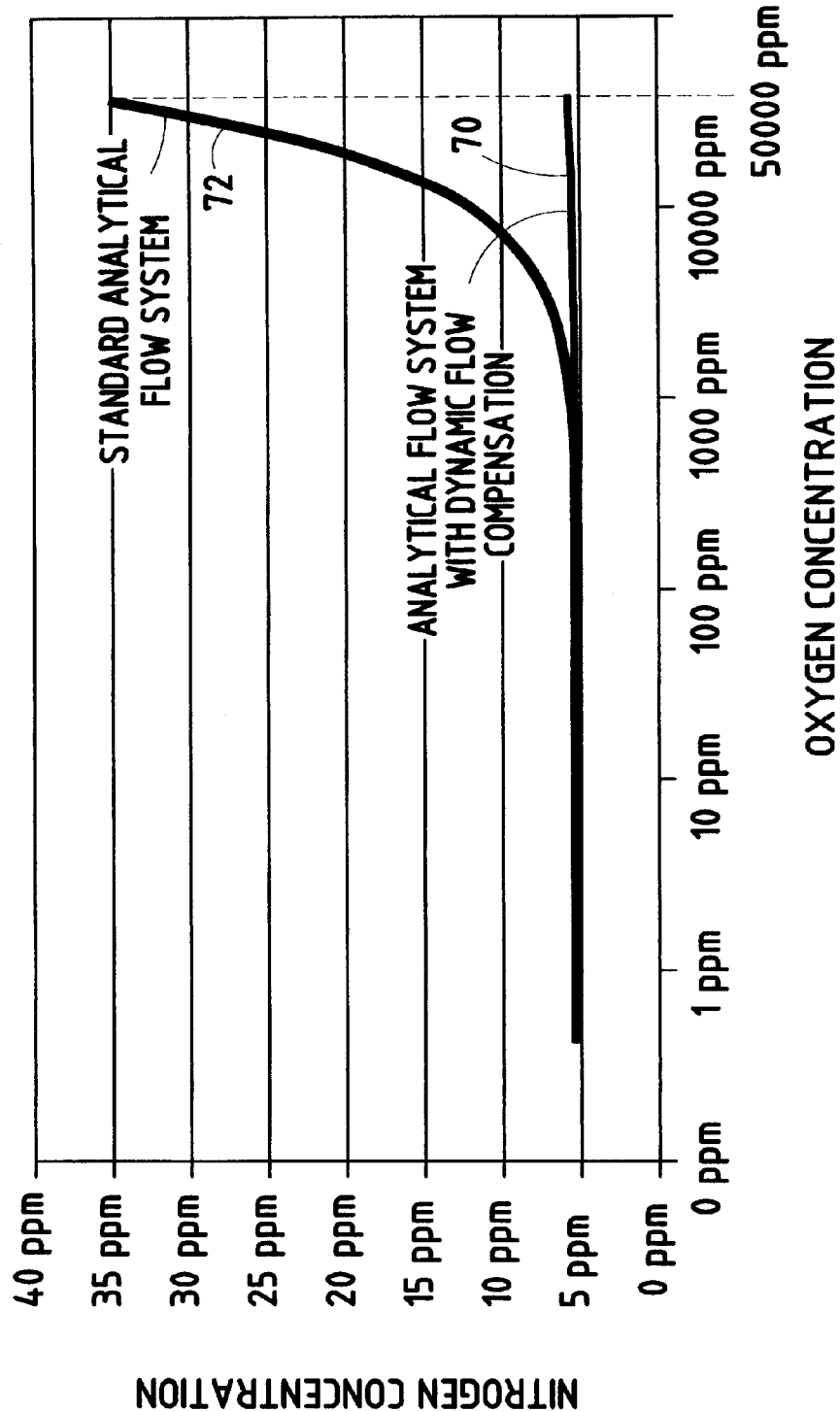
FIG. 6 is a diagram illustrating the analytical results when using an analyzer as shown in FIGS. 4 and 5 as compared to the use of prior art analyzers.

The results of this dynamic compensation are shown in FIG. 6 in which curve 70 represents the thermal conductivity detector 26 output signal for a 5 ppm concentration of nitrogen in the presence of varying amounts of oxygen concentration. As seen in FIG. 6, the measured concentration of the fixed small amount of nitrogen remains constant, allowing a small concentration of nitrogen to be accurately determined in the presence of relatively high concentrations of oxygen (i.e., up to 50,000 ppm). Graph 72 represents the prior art results of FIG. 1 where, when oxygen has a concentration of greater than about 500 ppm, the thermal conductivity detector erroneously provides a higher detected level of nitrogen in view of the dramatic pressure drop taking place in the system of FIG. 1 due to scrubbing of the carbon dioxide. The system of FIG. 3 provides results following between curves 70 and 72.

FIG. 5 illustrates an alternative embodiment of the present invention which provides substantially the same results as shown by curve 70 in FIG. 6. Instead of a pressure detector 66, a flow meter 76 provides an electrical output signal coupled by conductor 77 to a control 30 circuit 78 which provides an output signal to an electrically actuated flow control valve 74 to maintain the stream of gas through flow meter 76 constant at, for example, 460 cc per minute as the scrubber 22 responds to the amount of carbon dioxide being scrubbed from the gas stream from furnace 12. In this system as in the system of FIG. 4, the thermal conductivity cell 26 sees a constant flow rate of the mix of carrier gas and analyte, such as nitrogen, and responds by providing an accurate output reading for the presence of an analyte, such as nitrogen, present in the original sample of a high concentration of a second analyte, such as oxygen. In this system, nitrogen concentrations as low as about 0.05 ppm can be accurately detected. High concentrations of nitrogen above about 3,500 ppm are not subject to the errors for which compensation is required.

Although the system of the present invention has been described in connection with a nitrogen/oxygen analyzer where a relatively small amount of nitrogen is present resulting in inaccuracies when in the presence of higher concentrations of oxygen, the inert gas makeup system of the present invention can be employed in any type of analyzer where two or more analytes must be separated for detection and such separation normally would result in inaccuracies of the detection of a second analyte in the presence of a relatively large analyte scrubbed from the gas stream. Thus, the compensation system of this invention can be used in a CHN analyzer for organic samples where $H_2O$ is removed and $CO_2$ is scrubbed from the analyte stream. It can also be used in CHNS analyzers where $SO_2$ is scrubbed from the analyte stream.

It will become apparent to those skilled in the art that various modifications to the preferred embodiment of the invention as described herein can be made without departing from the spirit or scope of the invention as defined by the appended claims.

The invention claimed is:

1. An analyzer for the determination of the concentration of first and second analytes in a sample comprising:

a furnace for combusting a sample into gaseous byproducts of combustion;

a source of an inert carrier gas for sweeping the byproducts of combustion from said furnace to a detector for the detection of a first analyte;

a scrubber coupled to the detector for removing the first analyte from the inert gas stream;

a second detector coupled to the scrubber for detecting the second analyte;

a conduit coupled from said source of carrier gas to the junction of said scrubber and second detector;

a control valve coupled in said conduit between said source and said second detector;

a pressure transducer coupled to said conduit; and a control circuit coupled to said pressure transducer for detecting the pressure thereof and providing an output control signal applied to said control valve to maintain the pressure in the flow path between said scrubber and said second detector substantially constant by controlling the flow of inert gas from said source when the scrubber tends to lower the pressure due to relatively high concentrations of a first analyte as compared to the second analyte.

2. The analyzer as defined in claim 1 wherein said first analyte is oxygen having a concentration of from about 500 to about 50,000 ppm.

3. The analyzer as defined in claim 2 wherein said second analyte is nitrogen having a concentration of from about 0.05 ppm to about 3,500 ppm.

4. An analyzer for the determination of the concentration of first and second analytes in a sample comprising:

a furnace for combusting a sample into gaseous byproducts of combustion;

a source of an inert carrier gas for sweeping the byproducts of combustion from said furnace to a detector for the detection of a first analyte;

a scrubber coupled to the detector for removing the first analyte from the inert gas stream;

a second detector coupled to the scrubber for detecting the second analyte;

a conduit coupled from said source of carrier gas to the junction of said scrubber and second detector;

a control valve coupled in said conduit between said source and said second detector;

a flow meter coupled in said conduit between said scrubber and said second detector; and a control circuit coupled to said flow meter for detecting the flow rate in said conduit and providing an output control signal applied to said control valve to maintain the flow rate in the flow path between said scrubber and said second detector substantially constant by controlling the flow of inert gas from said source when the scrubber tends to lower the flow rate due to relatively high concentrations of a first analyte as compared to the second analyte.

5. The analyzer as defined in claim 4 wherein said first analyte is oxygen having a concentration of from about 500 to about 50,000 ppm.

6. The analyzer as defined in claim 5 wherein said second analyte is nitrogen having a concentration of from about 0.05 ppm to about 3,500 ppm.

7. A flow compensation system for an analyzer having an analytical furnace for the combustion and determination of the concentration of first and second analytes in a sample, comprising:

a furnace for providing gaseous byproducts from a sample;

first and second detectors for detecting the concentration of first and second analytes respectively, said detectors being connected in series to the outlet of said furnace;

a source of an inert carrier gas and a first conduit for transferring the gaseous byproducts of combustion from said furnace to said detectors for detection of said first and second analytes, said first conduit extending between said detectors;

a scrubber coupled to said first detector for removing selected gaseous products: wherein said second detector is coupled to said scrubber for detecting said second analyte;

a second conduit coupled from said source of carrier gas to said first conduit extending between said detectors;

a control valve coupled in said second conduit;

a sensor coupled to said first conduit, said sensor located between said detectors; and a control circuit coupled to said sensor for detecting one of the pressure and flow rate in said first conduit and providing an output control signal applied to said control valve to maintain the flow substantially constant during an analysis of a sample having a relatively high concentration of a first analyte as compared to the second analyte.

8. The system as defined in claim 7 wherein said first analyte is oxygen having a concentration of from about 500 to about 50,000 ppm.

9. The system as defined in claim 8 wherein said second analyte is nitrogen having a concentration of from about 0.05 ppm to about 3,500 ppm.

10. The system as defined in claim 7 wherein said sensor is a pressure transducer coupled to said conduit.

11. The system as defined in claim 7 wherein said sensor is a flow meter coupled in said first conduit.

12. The system as defined in claim 10 wherein said first analyte is oxygen having a concentration of from about 500 to about 50,000 ppm.

13. The system as defined in claim 12 wherein said second analyte is nitrogen having a concentration of from about 0.05 ppm to about 3,500 ppm.

14. The system as defined in claim 11 wherein said first analyte is oxygen having a concentration of from about 500 to about 50,000 ppm.

15. The system as defined in claim 14 wherein said second analyte is nitrogen having a concentration of from about 0.05 ppm to about 3,500 ppm.

* * * * *